United States Patent [19]
Wagatsuma et al.

[11] Patent Number: 4,786,633
[45] Date of Patent: Nov. 22, 1988

[54] CEPHALOSPORIN COMPOUNDS

[75] Inventors: Mitsuyoshi Wagatsuma, Urawa; Toyonari Oine, Nara; Totaro Yamaguchi, Urawa, all of Japan

[73] Assignee: Tanabe Seiyaku Co., Ltd., Osaka, Japan

[21] Appl. No.: 56,958

[22] Filed: Jun. 3, 1987

[30] Foreign Application Priority Data

Jun. 4, 1986 [JP] Japan .................. 61-130879

[51] Int. Cl.⁴ .................. C07D 501/36; A61K 31/545
[52] U.S. Cl. .................. 514/206; 514/204; 540/226; 540/227; 540/225
[58] Field of Search .................. 540/226, 227, 222; 514/204, 206

[56] References Cited

U.S. PATENT DOCUMENTS

| | | | |
|---|---|---|---|
| 4,258,041 | 3/1981 | O'Callaghan et al. | 424/246 |
| 4,547,494 | 10/1985 | Oine et al. | 514/204 |
| 4,576,938 | 3/1986 | Wagatsuma et al. | 424/246 |
| 4,598,075 | 7/1986 | Oine et al. | 540/225 |
| 4,598,154 | 7/1986 | Oine et al. | 540/225 |
| 4,727,071 | 2/1988 | Oine et al. | 514/206 |

FOREIGN PATENT DOCUMENTS 0101265 2/1984 European Pat. Off. .
60-226884 11/1985 Japan .
61-78792 4/1986 Japan .

*Primary Examiner*—Nicholas S. Rizzo
*Attorney, Agent, or Firm*—Birch, Stewart, Kolasch & Birch

[57] ABSTRACT

A cephalosporin compound of the formula:

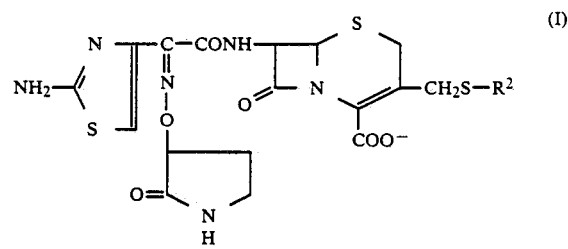

wherein:
$R^2$ is a group of the formula:

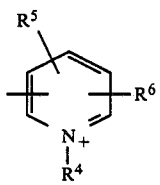

$R^4$ is a lower alkenyl group, a lower alkyl group or a lower alkyl group substituted with a member selected from the group consisting of cyano, lower alkylthio, 2-(lower alkyl)-1,3,4-thiadiazol-5-yl, carbamoyl, thiocarbamoyl, and N-lower alkyl(thiocarbamoyl) and $R^5$ and $R^6$ are each a hydrogen atom or a lower alkyl group, or a pharmaceutically acceptable salt thereof, is disclosed. These compounds have antimicrobial activity.

9 Claims, No Drawings

CEPHALOSPORIN COMPOUNDS

The present invention relates to a novel cephalosporin compound and processes for preparing the same.

Various cephalospolin antibiotics have been heretofore developed and the antimicrobial activity of these antibiotics are known to be greatly affected by the substituent at the 7-position or 3-position on the cephem ring.

It is an object of the present invention to provide a novel cephalosporin compound having a higher antimicrobial activity than the conventional cephalosporin antibiotics.

The present invention provides a novel cephalosporin compound represented by the formula

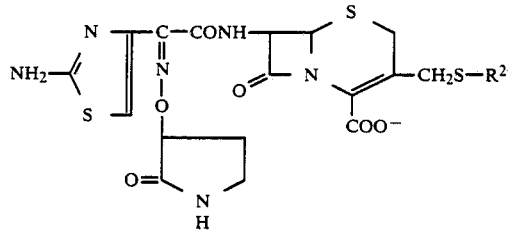

wherein:
$R^1$ is amino which may be protected,
$R^2$ is a substituted or unsubstituted heterocyclic group having 1 to 3 hetero atoms selected from the group consisting of nitrogen and sulfur, and
$R^3$ is carboxyl which may be protected or a group $-COO^-$.

The novel cephalosporin compound (I) of the present invention and a salt thereof exhibit potent antimicrobial activity against a wide variety of microorganisms including gram-positive and gram-negative bacteria and are useful as anti-bacterial agents. For example, the compound (I) and a salt thereof are useful as chemotherapeutic agents in mammals, including man, in the treatment of infectious diseases caused by the gram-positive and gram-negative bacteria, or as a supplement in animal feedstuffs.

The present invention provides a pharmaceutical composition for use as an antimicrobial agent which comprises the compound of the formula (I) or a salt thereof as an active ingredient together with a pharmaceutically acceptable carrier therefor.

The present invention also provides a method of treating microbial infections in a mammal which comprises administering to the mammal an antimicrobially effective amount of the compound (I) or a salt thereof.

Throughout the specification and the appended claims, the term "lower" used in conjunction with "alkyl," "alkoxy" and "alkenyl" except where noted otherwise is intended to indicate that the lower alkyl, alkoxy or alkenyl where it appears as such or in various groups has 1 to 4 carbon atoms. Thus, examples of lower alkyl groups are those having 1 to 4 carbon atoms such as methyl, ethyl, propyl, isopropyl, butyl, isobutyl, tert-butyl, and the like. Illustrative of lower alkoxy groups are those having 1 to 4 carbon atoms such as methoxy, ethoxy, propoxy, isopropoxy, butoxy, isobutoxy, tert-butoxy, and the like. Exemplary of lower alkenyl groups are those having 1 to 4 carbon atoms such as vinyl, allyl, 1-propenyl, butenyl, isopropenyl, and the like.

Throughout the specification and appended claims, the term "acyl" where it appears in various groups except where noted otherwise denotes an acyl having 1 to 5 carbon atoms and is intended to include formyl, alkylcarbonyl having an alkyl moiety with 1 to 4 carbon atoms, such as acetyl, propionyl, butyryl, pivaloyl, and the like.

A variety of heterocyclic groups are encompassed by the substituted or unsubstituted heterocyclic group $R^2$ in the formula (I) which has 1 to 3 hetero atoms selected from the group consisting of nitrogen and sulfur. Typical examples thereof are heterocyclic groups represented by the formulas:

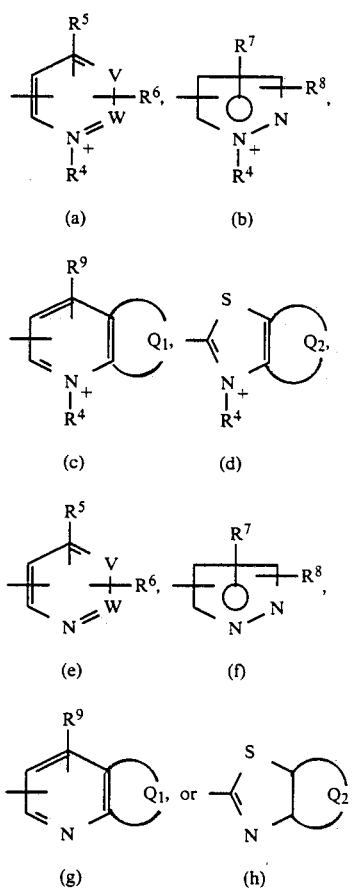

wherein:
$R^4$ is lower alkenyl, a nitrogen-containing 5- or 6-membered heterocyclic group optionally having a substituent, acylamino, or lower alkyl optionally having a substituent,
$R^5$ and $R^6$ are the same or different and each represent hydrogen, lower alkyl, amino, acylamino, carboxyl, carbamoyl, thiocarbamoyl or lower alkoxycarbonyl,
$R^7$, $R^8$ and $R^9$ are each lower alkyl,
V and W are the same or different and represent a group $-CH=$ or a group $-N=$, and
$Q_1$ and $Q_2$, each taken together with the two carbon atoms to which they are attached, form a 6-membered cyclic group which may optionally contain a nitrogen atom in its ring structure.

When $R^2$ is a heterocyclic group represented by any of the formulas (a) to (h), $R^3$ is preferably a group —COO⁻.

Examples of the substituted or unsubstituted 5- or 6-membered heterocyclic group containing nitrogen represented by $R^4$ are pyrrolyl, pyridyl, pyrazolyl, imidazolyl, oxopyrrolidinyl, and the like. Examples of the substituents which the lower alkyl group represented by $R^4$ may optionally have are cyano, hydroxyl, lower alkoxy, N-(lower alkyl)carbamoyloxy, carboxyl, amino, N,N-di(lower alkyl)amino, acylamino, (N-(lower alkyl)carbamoyl)amino, (N-(lower alkyl)thiocarbamoyl)amino, lower alkoxycarbonylamino, lower alkylthio, phenyl, carbamoylphenyl, 2-(lower alkyl)-1,3,4-thiadiazol-5-yl and a group represented by the formula

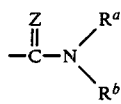

wherein:
$R^a$ and $R^b$ are the same or different and each represent hydrogen, lower alkyl, hydroxyl, amino or lower alkenyl, or $R^a$ and $R^b$, taken together with the nitrogen atom to which they are attached, may form a morpholino group and Z is an oxygen or a sulfur atom.

Examples of the 6-membered cyclic group which may optionally contain nitrogen and which are formed by $Q_1$ and $Q_2$, taken together with the two carbon atoms to which they are attached, are a cyclohexene ring (wherein $Q_1$ or $Q_2$ is tetramethylene), pyridine ring, pyrrole ring, and the like.

A preferred class of the compounds (I) are compounds wherein $R^1$ is as defined above, $R^2$ is a group of any of formulas (a) to (d), especially a group of the formula (a), and $R^3$ is a group —COO⁻.

A more preferred class of the compounds (I) are compounds wherein $R^1$ is as defined above, $R^2$ is a group represented by the formula

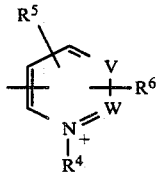

wherein:
$R^4$ is lower alkenyl, pyridyl, oxopyrrolidinyl, acylamino or optionally substituted lower alkyl wherein the substituent is selected from the group consisting of cyano, hydroxyl, lower alkoxy, N-(lower alkyl)carbamoyloxy, carboxyl, amino, N,N-di(lower alkyl)amino, acylamino, (N-(lower alkyl)carbamoyl)amino, (N-(lower alkyl)thiocarbamoyl)amino, lower alkoxycarbonylamino, lower alkylthio, phenyl, carbamoylphenyl, 2-(lower alkyl)-1,3,4-thiadiazol-5-yl and a group represented by the formula

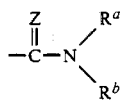

(wherein $R^a$ and $R^b$ are the same or different and each represent hydrogen, lower alkyl, hydroxyl, amino or lower alkenyl or $R^a$ and $R^b$, taken together with the nitrogen atom to which they are attached, form a morpholino group, and Z is oxygen or sulfur), $R^5$, $R^6$, V and W are as defined above, and $R^3$ is a group —COO⁻.

In the above preferred class of compound (I), the groups V and W in the formula (a) are preferably —CH=. In this case, the groups $R^5$ and $R^6$ are preferably both hydrogen.

Another preferred class of the compounds (I) are compounds wherein $R^1$ is as defined above, $R^2$ is a group represented by the formula

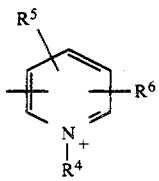

wherein:
$R^4$ is lower alkenyl, pyridyl, lower alkyl, N-(lower alkyl)carbamoyl-substituted lower alkyl or phenyl-substituted lower alkyl, $R^5$ and $R^6$ are as defined above, and $R^3$ is a group —COO⁻. When $R^2$ is a group (a'), $R^5$ and $R^6$ are preferably both hydrogen. In this case, $R^4$ is preferably lower alkenyl or lower alkyl.

In the compound (I), it is generally preferred that $R^1$ is amino.

While compounds of the formula (I) wherein $R^2$ represents a group of any of the formulas (e) to (h) exhibit antimicrobial activity, they are additionally useful as the intermediates for preparing the compound of the formula (I) wherein $R^3$ represents a group of any of the formulas (a) to (d).

In the compound of the formula (I) of the invention, when $R^1$ is a protected amino group, a wide variety of protecting groups which have been usually employed to protect amino group in the peptide synthesis can be used for protecting the amino group. Examples of such protecting groups include lower alkanoyl such as formyl, acetyl and pivaloyl; mono-, di- or trihalogeno-lower alkanoyl such as chloroacetyl and trifluoroacetyl; lower alkoxycarbonyl such as methoxycarbonyl, ethoxycarbonyl and tert.-butoxycarbonyl; substituted or unsubstituted benzyloxycarbonyl such as benzyloxycarbonyl and p-methoxybenzyloxycarbonyl; substituted or unsubstituted phenyl-lower alkyl such as p-methoxybenzyl and 3,4-dimethoxybenzyl; and di- or triphenyl lower alkyl such as benzhydryl and trityl.

On the other hand, when $R^4$ is a protected carboxyl group, the protecting group for the carboxyl group should preferably be one which can be easily removed in a conventional manner such as hydrolysis, acid treatment or reduction. Examples of such protecting groups include lower alkyl such as methyl, ethyl or tert-butyl; substituted or unsubstituted phenyl-lower alkyl such as benzyl, p-methoxybenzyl and p-nitrobenzyl; benzhydryl; tri-lower alkylsilyl such as trimethylsilyl; and the like.

In the compound of the invention, the oxyimino moiety represented by the formula

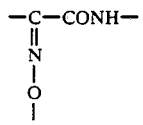

is intended to include each of the geometric isomers having the moiety of the formulas

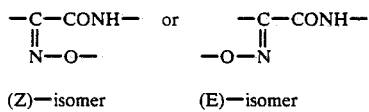

or a mixture of such geometric isomers unless otherwise specified. However, when used as a medicament, the compound (I) of the invention is preferably a compound wherein the configuration of the oxyimino moiety is Z (i.e., syn)-configuration. Although the Z (i.e., syn)-isomers of the compound (I) exhibit the best biological properties, they may coexist with small amounts of E (i.e., anti)-isomer.

According to the present invention, the contemplated compound (I) or a salt thereof may be prepared by the steps of:

(A) condensing an oxyiminoacetic acid compound of the formula

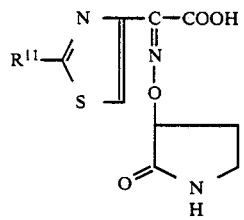 (II)

wherein $R^{11}$ is an optionally protected amino group, or a salt or a reactive derivative thereof with a 7-aminocephalosporin compound of the formula

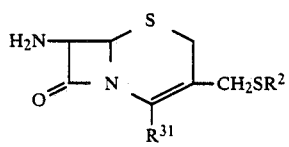 (III)

wherein $R^{31}$ is an optionally protected carboxyl group or a group —COO⁻ and $R^2$ is as defined above, or a salt thereof, or (B) condensing a cephalosporin compound of the formula

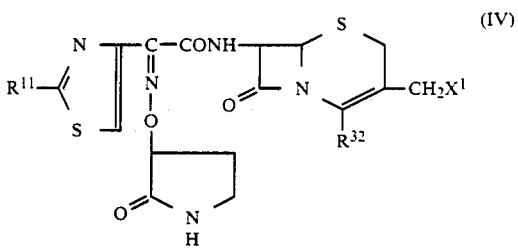 (IV)

wherein $R^{11}$ is as defined above, $R^{32}$ is an optionally protected carboxyl group and $X^1$ is a reactive residue, or a salt thereof with a thiol compound of the formula $R^2$—SH (V)

wherein $R^2$ is as defined above, or a salt thereof, and (C) when $R^{11}$ is a protected amino group and/or $R^{31}$ or $R^{32}$ is a protected carboxyl group, removing the protecting group therefrom if so desired, and (D) if desired, subjecting the product obtained above to a salt-forming reaction.

Of the contemplated compounds (I), those wherein $R^2$ is a group represented by one of the foregoing formulas (a) through (d) (hereinafter referred to as "compounds (I-a)" can also be prepared by reacting the contemplated compound (I) wherein $R^2$ is a group represented by one of the foregoing formulas (e) through (h) (hereinafter referred to as "compounds (I-b)" or a salt thereof with a compound of the formula $R^4$—$X^2$ (VI)

wherein $R^4$ is a defined above and $X^2$ is a reactive residue, and when $R^1$ is a protected amino group and/or $R^3$ is a protected carboxyl group, removing the protecting group therefrom if so desired.

Further, of the contemplated compounds (I), those represented by the formula

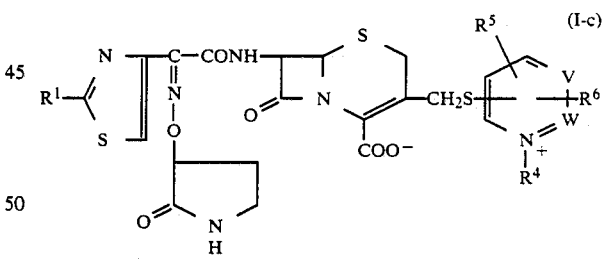 (I-c)

wherein V, W, $R^1$, $R^4$, $R^5$ and $R^6$ are as defined above or a salt thereof can also be prepared by reacting the foregoing cephalosporin compound (IV) or a salt thereof with a thioketone compound of the formula

 (VII)

wherein V, W, $R^4$, $R^5$ and $R^6$ are as defined above, and when $R^{11}$ is a protected amino group and/or $R^{32}$ is a protected carboxyl group, removing the protecting group if so desired.

Suitable examples of the salt of the starting materials (II), (III) and (IV) useful in the invention are, for example, inorganic salts such as sodium or potassium salts or organic amine salts such as triethylamine salts or triethylamine salts. The compound (I-b) can also be used in the form of such salts. On the other hand, preferable examples of the salt of the starting material (V) are, for example, alkali metal salts such as sodium or potassium salt. In the compounds (I-a), (II), (III) and (IV), when $R^{11}$ is a protected amino group and/or $R^{31}$ or $R^{32}$ is a protected carboxyl group, the protecting groups may be any of the protecting groups described with respect to $R^1$ and $R^3$.

While the oxyiminoacetic acid compound (II) can exist in the form of two optical isomers due to the asymmetric carbon atom involved in the oxopyrrolidine group, either an optical isomer of the compound (II) or a racemic mixture thereof may be used for the purpose of the present invention.

The condensation reaction of the oxyiminoacetic acid compound (II), a salt thereof or a reactive derivative thereof with the 7-aminocephalosporin compound (III) or a salt thereof can be easily carried out in a conventional manner. For example, the condensation of the oxyiminoacetic acid compound (II) in its free form with the 7-aminocephalosporin compound (III) can be conducted in the presence of a dehydrating agent in a suitable solvent. Suitable examples of the dehydrating agent are dicyclohexylcarbodiimide, N-ethyl-N'-(3-dimethylaminopropyl)carbodiimide, phosphorus oxychloride, phosphorus trichloride, thionyl chloride, oxalyl chloride, triphenylphosphine and the like. Vilsmeier reagent prepared from dimethylformamide and phosphorus oxychloride, from dimethylformamide and oxalyl chloride, from dimethylformamide and phosgene or from dimethyl-formamide and thionyl chloride may also be used as the dehydrating agent. Examples of useful solvent are dioxane, tetrahydrofuran, acetonitrile, chloroform, methylene chloride, dimethylformamide, N,N-dimethyl-acetamide, ethyl acetate, pyridine, ethanol, water and the like. It is suitable to conduct the reaction at a temperature of −50° to 50° C., preferably −30° to 20° C.

The condensation reaction of the reactive derivative of the oxyiminoacetic acid compound (II) with the 7-aminocephalosporin compound (III) or a salt thereof can be performed either in the presence or absence of an acid acceptor in a suitable solvent. Examples of the reactive derivative of the oxyiminoacetic acid compound (II) include the corresponding acid halides (e.g., acid chloride, acid bromide), and anhydrides, mixed anhydrides (e.g., a mixed anhydride of the oxyiminoacetic acid compound (II) and alkyl carbonate), active esters (e.g., p-nitrophenyl ester, 2,4-dinitrophenyl ester, succinimide ester, phthalimide ester, benzotriazole ester, 2-pyrrolidon-1-yl ester), acid azide, acid amides (e.g., imidazole amide, 4-substituted-imidazole amide, triazole amide) and so on. Usable as the solvent are dioxane, tetrahydrofuran, acetonitrile, chloroform, methylene chloride, dimethylformamide, N,N-dimethylacetamide, ethyl acetate, pyridine, acetone, water and the like. Suitable examples of the acid acceptor to be used when required are alkali metal hydroxides (e.g., sodium hydroxide and potassium hydroxide), alkali metal carbonates (e.g. sodium carbonate and potassium carbonate), alkali metal hydrogencarbonates (e.g., sodium hydrogencarbonate and potassium hydrogencarbonate), trialkylamines (e.g., trimethylamine and triethylamine), N,N-dialkylanilines (e.g., N,N-dimethylaniline and N,N-diethylaniline), pyridine, N-alkyl-morpholines (e.g., N-methylmorpholine) and so forth. It is suitable to conduct the reaction at a temperature of −50° to 50° C., preferably −30° to 20° C.

The condensation of the cephalosporin compound (IV) or a salt thereof with the thiol compound (V) or a salt thereof, and the reaction of the cephalosporin compound (IV) or a salt thereof with the thioketone compound (VII) can be properly effected in a solvent. Useful cephalosporin compounds (IV) include those wherein the reactive residue $X^1$ is carbamoyloxy group, an acyloxy group such as acetyloxy, propionyloxy, 3-oxobutyryloxy, 3-carboxypropionyloxy, 2-carboxybenzoyloxy, 4-carboxybutyryloxy, 2-(carboethoxycarbamoyl)bezoyloxy, 2-(carboethoxysulfamoyl)benzoyloxy, 3-ethoxycarbamoylpropionyloxy and the like; or a halogen atom such as bromine, chlorine and the like. It is preferred to conduct the reaction in a solvent. Examples of useful solvents are water, heavy water and an organic solvent which can be easily mixed with water and which will not react with the starting compounds, such as dimethylformamide, dimethylacetamide, dioxane, acetone, alcohol, acetonitrile, dimethyl sulfoxide, tetrahydrofuran, etc. The reaction is conducted at a temperature which is suitably determined over the range of 0° to 100° C., although variable depending on the kinds of starting materials and solvents used and other factors. It is desirable to perform the reaction at or around a pH in neutral range, specifically 2 to 8, preferably 5 to 8. The progress of the reaction can be made more smooth by adding to the reaction system a quaternary ammonium salt having a surface activity such as trimethylbenzyl ammonium bromide, triethylbenzyl ammonium bromide, triethylbenzyl ammonium hydroxide and the like; alkali metal halide such as sodium iodide, potassium iodide and the like; sodium hydrogencarbonate or phosphoric acid buffer solution; etc. Advantageous results can be obtained by carrying out the reaction in an atmosphere of inert gas such as nitrogen or argon to prevent air oxidation of the thiol compound (V) or thioketone compound (VII).

The reaction of the compound (I-b) or a salt thereof with the compound (VI) can be suitably performed in a solvent. Examples of the compound (VI) include compounds wherein the reactive residue $X^2$ is halogen atom such as chlorine, bromine, iodine or a lower alkylsulfonyl group such as mesyl or an arylsulfonyl group such as tosyl. Examples of suitable solvents are water, dimethylformamide, dimethylacetamide, dioxane, acetone, alcohol, acetonitrile, dimethylsulfoxide, tetrahydrofuran, mixtures thereof, etc. The reaction can smoothly proceed at a temperature of 0° to 70° C.

When the reaction produces the contemplated compounds (I), (I-a), (I-b) and (I-c) wherein $R^1$ (or $R^{11}$) is the protected amino group and/or $R^3$ (or $R^{31}$, $R^{32}$) is the protected carboxyl group, the protecting group or groups on the amino or carboxyl group may be removed from the compound thus obtained, when required. The removal of the protecting group or groups from the compound can be conducted by a conventional method such as hydrolysis, solvolysis, acid treatment or reduction. For example, when the protecting group on the amino group is formyl, acetyl, tert-butoxy carbonyl, trityl or benzhydryl and the protecting group on the carboxyl group is tert-butyl, p-methoxybenzyl or benzhydryl, the protecting group or groups can be removed by treating the compound with an acid such as trifluoroacetic acid, benzenesulfonic acid, p-toluenesulfonic acid, formic acid, hydrochloric acid, hyrogen bromide or the like. When the protecting group on the amino group is benzyloxycarbonyl, p-methoxybenzyloxycarbonyl, benzyl, p-methoxybenzyl or 3,4-dimethoxybenzyl, and the protecting group on the carboxyl group is benzyl, p-methoxybenzyl or p-nitrobenzyl, the removal of the protecting group or groups can be effected by a catalytic reduction of the compound in hydrogen gas in the presence of a catalyst such as palladium-barium carbonate, palladium-carbon or palladium-black. When the protecting group on the amino group is trifluoroacetyl, pivaloyl, methoxycarbonyl or ethoxycarbonyl, and the protecting group on the carboxyl group is methyl or ethyl, the protecting group or groups can be removed by hydrolysis of the compound using an alkali agent (e.g., sodium hydroxide or potassium hydroxide) or an acid (e.g., hydrochloric acid, hydrobromic acid). Further, when the protecting group on the amino group is chloroacetyl, the protecting group can be removed by the treatment with thiourea.

A salt of the contemplated compound (I) can be prepared by a conventional method, for example, by treating the compound (I) with an equimolar quantity of aqueous alkaline or acidic solution.

The starting compound (II) of the present invention can be prepared, for example, by the process disclosed in European patent publication No. 147,181. The starting compound (III) can be prepared, for example, by condensation of 7-aminocephalosporanic acid or a salt thereof with the compound (V). The reaction can be conducted under the same conditions as those described above for the reaction of the compound (IV) or a salt thereof with the compound (V) or a salt thereof. The starting compound (IV) can be prepared, for example, in accordance with the process disclosed in European patent publication No. 147,181 by condensing the compound (II) in a conventional manner with a 7-aminocephalosporin compound represented by the formula

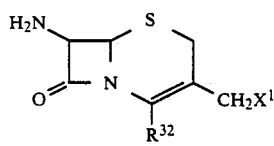

wherein $R^{32}$ and $X^1$ are as defined above.

The contemplated compound (I) of the present invention and salts thereof exhibit potent antimicrobial activity against a wide variety of microorganisms including those belonging to the genera Streptococcus (e.g., St. pneumoniae), Enterococcus (e.g., E. faecalis), Staphylococcus (e.g., S. aureus., S. epidermidis), and Pseudomonas (e.g., Ps. aeruginosa) and the like, and are characterized by their potent antimicrobial activity against both gram-positive and gram-negative bacteria. The contemplated compound (I) and salts thereof also display potent antimicrobial activity against bacteria belonging to the genera Bacillus (e.g., B. subtilis), Escherichia (e.g., E. coli), Klebsiella (e.g., K. pneumoniae), Enterobacter (e.g., E. aerogenes, E. cloacae), Serratia (e.g., S. marcescens) and the like and against bacteria belonging to the genera Citrobacter, Proteus, Shigella, Haemophilus and Salmonella. Further the contemplated compound (I) and salts thereof show potent protective effects against microbial infections of various bacteria including Staphylococcus aureus and Pseudomonas aeruginosa because of the high absorbability or long-standing therapeutic effects in living tissues, and are characterized in that they have a higher antimicrobial activity in vivo than in vitro. The contemplated compound (I) and salts thereof have a high stability against a variety of β-lactamase-producing microorganisms, for example against β-lactamases produced by Proteus vulgaris. In addition, the contemplated compound (I) and salts thereof are low in toxicity and thus highly safe as pharmaceuticals.

The contemplated compound (I) of the present invention can be used for pharmaceutical applications either in the free form or in the form of a salt thereof. Pharmaceutically acceptable salts of the compound (I) include, for example, non-toxic metallic salts such as sodium, potassium, calcium, magnesium and aluminum salts; salts thereof with non-toxic amines such as trialkylamines (such as triethylamine), pyridine, ethanolamine, triethanolamine, dicyclohexylamine or the like; salts thereof with inorganic acids such as hydrochloric acid, sulfuric acid or hydrobromic acid or the like; salts thereof with organic acids such as oxalic acid, tartaric acid or the like; addition salts thereof with amino acids such as glycine, lysine, arginine, aspartic acid, glutamic acid or the like; and so on. These salts may be those with resins including, for example, a polystyrene resin containing an amino group, a quaternary amino group or sulfonic acid group or resin containing a carboxy group (e.g., polyacrylic resin) or may be complexes with metal salts such as an iron or copper salt, or with ammonium salts such as ammonium chloride. Accordingly the contemplated compound (I) of the present invention and salts thereof should be interpreted as including inner salts, addition products, complexes, solvates and hydrates thereof.

The contemplated compound (I) or a salt thereof can be administered either orally or parenterally (e.g., intravenously, intramuscularly, subcutaneously). The daily dose of the compound (I) or a salt thereof may vary over a wide range depending on the age, body weight, conditions of patients, and severity of diseases to be treated. In general, however, a daily dose of the compound (I) or a salt thereof may be about 0.002 to about 0.2 g, preferably about 0.01 to about 0.04 g, per kg of body weight per day. Further the contemplated compound (I) or a salt thereof may be used in the form of a pharmaceutical preparation containing the same compound in association or admixture with pharmaceutical excipients suitable for oral or parenteral administration. Suitable excipients include, for example, gelatin, lactose, glucose, sodium chloride, starch, magnesium stearate, talc, vegetable oil and other known medicinal excipients. The pharmaceutical preparations may be in solid form such as tablets, granules or capsules; or in liquid form such as solutions, suspensions or emulsions. They may be sterilized and/or may further contain auxiliaries such as stablizing, wetting or emulsifying agents.

Experimental Example

Experimental method (Antimicrobial activity in vitro)

The minimum inhibitory concentration (MIC, μg/ml) of a test compound was determined by means of a standard agar plate dilution method (based on the standard method of Japan Society of Chemotherapy). Media used in the experiment were Mueller-Hinton agar (MHA; product of Nissui).

(Protective effects on bacterial infections in mice)

Ten mice weighing 20±1 g were used for each dose level. Mice were challenged via the intraperitoneal route with sufficient bacteria to kill all non-treated mice within 24 hours. All bacteria were suspended in a physiological saline solution containing 6% mucin. A test compound was administered intramuscularly one hour after the infection. Survival ratios were determined 7 days after the infection. The median effective doses ($ED_{50}$, mg/kg) of the test compound were estimated by the probit analysis.

Table I below shows the results.

TABLE I

| Test compound* | | Microorganisms tested | |
|---|---|---|---|
| | | Staphylococcus aureus Smith | Pseudomonas aeruginosa PI-67 |
| 1 | M.I.C. (μg/ml) | 0.78 | 0.78 |
| | $ED_{50}$ (mg/kg) | 0.14 | 12.3 |
| 2 | M.I.C. (μg/ml) | 0.78 | 1.56 |
| | $ED_{50}$ (mg/kg) | 0.25 | 15.8 |
| 3 | M.I.C. (μg/ml) | 1.56 | 3.13 |
| | $ED_{50}$ (mg/kg) | 0.40 | 10.8 |

*Test Compound 1: 7β-{(Z)—2-(2-aminothiazol-4-yl)-2-[((3S)—2-oxopyrrolidin-3-yl)oxyimino]-acetamido}-3-(1-methyl-4-pyridinio)-thiomethyl-3-cephem-4-carboxylate
Test Compound 2: 7β-{(Z)—2-(2-aminothiazol-4-yl)-2-[((3S)—2-oxopyrrolidin-3-yl)oxyimino]-acetamido}-3-(1-methyl-2-pyridinio)-thiomethyl-3-cephem-4-carboxylate
Test Compound 3: 7β-{(Z)—2-(2-aminothiazol-4-yl)-2-[((3S)—2-oxopyrrolidin-3-yl)oxyimino]-acetamido}-3-(1-allyl-2-pyridinio)-thiomethyl-3-cephem-4-carboxylate

EXAMPLE 1

To 6 ml of water are added 337 mg of 7β-{-(Z)-2-(2-aminothiazol-4-yl)-2-[((3S)-2-oxopyrrolidin-3-yl)oxyimino]acetamido}-3-acetoxymethyl-3-cephem-4-carboxylic acid, 84 mg of 1-methyl-4-thiopyridone, 77 mg of sodium hydrogencarbonate and 898 mg of sodium iodide. The mixture is stirred in an argon atmosphere at 61° C. for 6 hours. The reaction mixture is concentrated under reduced pressure. The concentrate is introduced into a column packed with a non-ionic adsorbent resin (tradename: Diaion HP-20, product of Mitsubishi Chemical Indiustries, Limited, hereinafter referred to as "HP-20") and is eluted with 20% methanol. The fractions containing the contemplated compound are collected and concentrated. The residue is lyophilized, giving 85 mg of 7β-{(Z)-2-(2-aminothiazol-4-yl)-2-[((3S)-2-oxopyrrolidin-3-yl)oxyimino]acetamido}-3-(1-methyl-4-pyridinio)thiomethyl-3-cephem-4-carboxylate as a pale yellow compound.

m.p. >170° C. (decomp.).

Mass (m/e): 590 $(M+1)^+$.

IR $v_{max}^{Nujol}$ ($cm^{31\ 1}$): 3310, 1700, 1690, 1630, 1600, 1530.

NMR ($D_2O$) δ: 2.1–2.8 (2H, m), 3.5 (2H, m), 3.49 and 3.80 (2H, each d, J=17 Hz), 4.21 (3H, s), 4.21 and 4.43 (2H, each d, J=14 Hz), 5.10 (1H, t, J=8 Hz), 5.24 (1H, d, J=4 Hz), 5.78 (1H, d, J=4 Hz), 7.07 (1H, s), 7.83 (2H, d, J=7 Hz), 8.39 (2H, d J=7 Hz).

EXAMPLE 2

To 4.8 ml of water are added 341 mg of 7β{(Z)-2-(2-aminothiazol-4-yl)-2-[((3S)-2-oxopyrrolidin-3-yl)oxyimino]acetamido}-3-acetoxymethyl-3-cephem-4-carboxylic acid, 125 mg of 1-methyl-2-thiopyridone and 900 mg of sodium iodide. The mixture is adjusted to a pH of 6.63 with an aqueous solution of sodium hydrogencarbonate. The mixture is stirred in an argon atmosphere at 65° C. for 3.5 hours. The reaction mixture is concentrated under reduced pressure. The concentrate is introduced into a column packed with HP-20 and is eluted with 20% and 25% methanol solutions. The fractions containing the contemplated compound are collected and concentrated. The residue is lyophilized, giving 128 mg of 7β-{(Z)-2-(2-aminothiazol-4-yl)-2-[((3S)-2-oxopyrrolidin-3-yl)oxyimino]acetamido}-3-(1-methyl-2-pyridinio)thiomethyl-3-cephem-4-carboxylate as a pale brown compound.

m.p. >230° C. (decomp.).

Mass (m/e): 590 $(M+1)^+$.

IR $v_{max}^{Nujol}$ ($cm^{-1}$): 3350, 3200, 1770, 1690, 1600, 1560, 1540.

NMR ($D_2O$) δ: 2.1–2.8 (2H, m), 3.5 (2H, m), 3.62 (2H, m), 4.27 (3H, s), 4.31 and 4.56 (2H, each d, J=13 Hz), 5.11 (1H, t, J=7 Hz), 5.22 (1H, d, J=5 Hz), 5.80 (1H, t, J=5 Hz), 7.08 (1H, s), 7.73 (1H, t, J=6.3 Hz), 7.97 (1H, d, J=8 Hz), 8.33 (1H, dd, J=6.3 and 8 Hz) 8.70 (1H, d, J=6.3 Hz)

The following compound is prepared by the same procedure as described above.

7β-{(Z)-2-(2-aminothiazol-4-yl)-2-[((3S)-2-oxopyrrolidin-3-yl)oximino]acetamido}-3-(1-(N-methylcarbamoylmethyl)-2-pyridinio)thiomethyl-3-cephem-4-carboxylate m.p. 155°–165° C. (colored and decomp.).

Mass (m/e): 647 $(M+1)^+$.

IR $v_{max}^{Nujol}$($cm^{-1}$: 3320, 1770, 1680, 1610, 1560, 1530.

NMR ($D_2O$) δ: 2.54 (2H, m), 2.93 (2H, s), 3.58 (2H, m), 3.51 and 3.82 (2H, each d, J=18 Hz), 4.40 and 4.62 (2H, each d, J=13 Hz), 5.15 (1H, t, J=7 Hz), 5.28 and 5.84 (2H, each d, J=4.6 Hz), 5.57 (2H, s), 7.17 (1H, s), 8.53 (1H, t, J=7 Hz), 8.80 (1H, d, J=7 Hz)

EXAMPLE 3

To a mixture of 4.8 ml of water and 1.5 ml of acetonitrile are added 710 mg of sodium 7β-{(Z)-2-(2-aminothiazol-4-yl)-2-[((3S)-2-oxopyrrolidin-3-yl)oxyimino]acetamido}-3-acetoxymethyl-3-cephem-4-carboxylate, 302 mg of 1-allyl-2-thiopyridone and 1800 mg of sodium iodide. The mixture is adjusted to a pH of 6.80 with a diluted aqueous solution of acetic acid. Subsequently the mixture is treated in the same manner as described in Example 2, producing 100 mg of 7β-{(Z)-2-(2-aminothiazol-4-yl)-2-[((3S)-2-oxopyrrolidin-3-yl)oxyimino]acetamido}-3-(1-allyl-2-pyridinio)thiomethyl-3-cephem-4-carboxylate as a pale brown compound.

m.p. >250° C. (decomp.).

Mass (m/e): 616 $(M+1)^+$.

IR $v_{max}^{Nujol}$ ($cm^{-1}$): 3350, 3200, 1770, 1690, 1610, 1560, 1540.

NMR ($D_2O$) δ: 2.1–2.8 (2H, m), 3.5 (2H, m), 3.50 and 3.81 (2H, each d, J=18 Hz), 4.30 and 4.59 (2H, each d, J=13 Hz), 5.11 (1H, t, J=8 Hz), 5.22 (1H, d, J=4.5 Hz), 5.40 (4H, m), 5.80 (1H, d, J=4.5 Hz), 6.11 (1H, m), 7.15

(1H, s), 8.76 (1H, d, J=5.8 Hz), 7.81 (1H, t, J=5.8 Hz), 8.04 (1H, d, J=8 Hz), 8.38 (1H, dd, J32 5.8 and 8 Hz).

The following compound is prepared in the same manner as described above.

7β{(Z)-2-(2-aminothiazol-4-yl)-2-[((3S)-2-oxopyrrolidin-3-yl)oxyimino]acetamido}-3-(1-allyl-4-pyridinio)-thiomethyl-3-cephem-4-carboxylate m.p. >165° C. (decomp.).

IR $\nu_{max}^{Nujol}$ (cm$^{-1}$): 3340, 1770, 1690, 1620, 1600.

NMR (D$_2$O) δ: 2.2–2.8 (2H, m), 3.4–3.6 (2H, m), 3.49 and 3.80 (2H, each d, J=18 Hz), 4.21 and 4.27 (2H, each d, J=13 Hz), 5.06 (2H, d, J=8 Hz), 5.10 (1H, t, J=8 Hz), 5.23 (1H, d, J=5 Hz), 5.45 (1H, d, J=17 Hz), 5.55 (1H, d, J=10 Hz), 5.80 (1H, d, J=5 Hz), 5.9–6.4 (1H, m), 7.06 (1H, s), 7.87 (2H, d, J=6 Hz), 8.46 (2H, d, J=6 Hz)

EXAMPLE 4

To 20 ml of water are added 682 mg of 7β-{(Z)-2-(2-aminothiazol-4-yl)-2-[((3S)-2-oxopyrrolidin-3-yl)oxyimino]acetamido}-3-acetoxymethyl-3-cephem-4-carboxylic acid, 300 mg of 1-benzyl-4-thiopyridone, 1.8 g of sodium iodide and 110 mg of sodium hydrogencarbonate. The mixture is adjusted to a pH of 6.6 with an aqueous solution of sodium hydrogencarbonate. The mixture is stirred in an argon atmosphere at 70° C. for 1.5 hours. The mixture is subsequently treated in the same manner as described in Example 2, giving 270 mg of 7β-{(Z)-2-(2-aminothiazol-4-yl)-2-[((3S)-2-oxopyrrolidin-3-yl)oxyimino]acetamido}-3-(1-benzyl-4-pyridinio)thiomethyl-3-cephem-4-carboxylate.

m.p. 170°–185° C. (decomp.).

IR $\nu_{max}^{Nujol}$ (cm$^{-1}$): 3350, 1770, 1690, 1625, 1595.

NMR (D$_2$O) δ: 2.5 (2H, m), 3.5 (2H, m), 3.46 and 3.74 (1H, each d, J=18 Hz), 4.31 and 4.52 (1H, each d, J=13 Hz), 5.04 (1H, d, J=7.8 Hz), 5.18 (1H, d, J=4.4 Hz), 5.68 (2H, s), 5.77 (1H, d, J=4.4 Hz), 7.02 (1H, s), 7.56 (5H, s), 7.97 (2H, d, J=6.5 Hz), 8.64 (2H, d, J=6.5 Hz).

EXAMPLE 5

To 15 ml of water are added 682 mg of 7β-{(Z)-2-(2-aminothiazol-4-yl)-2-[((3S)-2-oxopyrrolidin-3-yl)oxyimino]acetamido}-3-acetoxymethyl-3-cephem-4-carboxylic acid, 225 mg of 1-(4-pyridyl)-4-thiopyridone, 2 g of sodium iodide and 120 mg of sodium hydrogencarbonate. The mixture is adjusted to a pH of 6.7 with an aqueous solution of sodium hydrogencarbonate. The mixture is stirred in an argon atmosphere at 70° C. for 12 hours. Subsequently the mixture is treated in the same manner as described in Example 2, producing 290 mg of 7β-{(Z)-2-(2-aminothiazol-4-yl)-2-[((3S)-2-oxopyrrolidin-3-yl)oxyimino]acetamido}-3-(1-(4-pyridyl)-4-pyridinio)thiomethyl-3-cephem-4-carboxylate.

m.p. 160°–175° C. (decomp.).

IR $\nu_{max}^{Nujol}$ (cm$^{-1}$): 3350, 1770, 1690, 1625, 1590.

NMR (D$_2$O) δ: 2.5 (2H, m), 3.5 (2H, m), 3.53 and 3.82 (1H, each d, J=18 Hz), 4.44 (2H, broad s), 5.07 (1H, t, J=7.7 Hz), 5.27 (1H, d, J=4.6 Hz), 5.78 (1H, d, J=4.6 Hz), 6.99 (1H, s), 7.85 (2H, d, J=6.3 Hz), 8.10 (2H, d, J=7 Hz), 8.79 (2H, d, J=7 Hz), 8.90 (2H, d, J=6.3 Hz).

EXAMPLE 6

In a mixture of 0.5 ml of water and 5 ml of dimethylformamide is dissolved 600 mg of potassium 7β-{(Z)-2-(2-aminothiazol-4-yl)-2-[((3S)-2-oxopyrrolidin-3-yl)oxyimino]acetamido} - 3 - (4 - pyridyl)thiomethyl - 31 - cephem-4-carboxylate obtained in Example 65 to be described later. To the solution are added 46 mg of formic acid and 710 mg of methyl iodide. The mixture is stirred at room temperature for 10 hours and the resulting mixture is concentrated under reduced pressure, followed by addition of an acetone-ether mixture to the residue. Insolubles are removed by filtration and the filtrate is purified by chromatography on a column packed with HP-20, giving 7β-{(Z)-2-(2-aminothiazol-4-yl) - 2 - [((3S) - 2 - oxopyrrolidin-3-yl)oxyimino]acetamido} - 3 - (1 - methyl - 4 - pyridinio)thiomethyl-3-cephem-4-carboxylate.

The reaction product thus obtained is identical in physicochemical properties with the product prepared in Example 1.

EXAMPLES 7 TO 67

The corresponding starting compounds are treated in the same manner as in Examples 1 to 5 and the compounds as listed below in Tables 1 and 2 are obtained.

The compounds obtained below are all in Z (i.e., syn)-configuration and 2-oxopyrrolidine moieties thereof are in (3S)-configuration.

TABLE 1

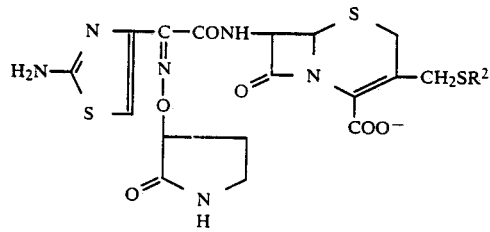

| Ex. No. | R$^2$ | Properties |
|---|---|---|
| 7 | 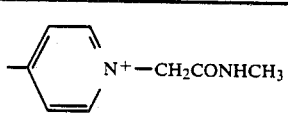 | m.p. 183–190° C. (decomp.)<br>IR $\nu_{max}^{Nujol}$ (cm$^{-1}$): 3250, 1760, 1670, 1620, 1590, 1530 |
| 8 | 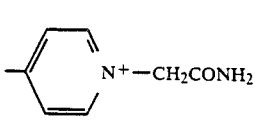 | m.p.: >185° C. (decomp.)<br>Mass (m/e): 633 (M + 1)$^+$<br>IR $\nu_{max}^{Nujol}$ (cm$^{-1}$): 3340, 3200, 1765, 1690, 1630, 1600 |

TABLE 1-continued

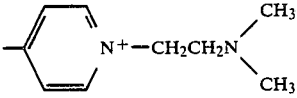

| Ex. No. | R² | Properties |
|---|---|---|
| 9 | 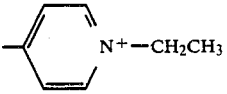 —N⁺—CH₂CH₂N(CH₃)₂ pyridinium | m.p. 160° C. (decomp.)<br>IR $\nu_{max}^{Nujol}$ (cm⁻¹): 3300, 1765, 1690, 1625, 1600 |
| 10 | —N⁺—CH₂CH₃ pyridinium | m.p. 170–185° C. (decomp.)<br>IR $\nu_{max}^{Nujol}$ (cm⁻¹): 3300, 1765, 1690, 1625, 1600 |
| 11 | —N⁺—CH₂CH₂CH₃ pyridinium | m.p. 165–177° C. (decomp.)<br>IR $\nu_{max}^{Nujol}$ (cm⁻¹): 3300, 1765, 1690, 1625, 1600 |
| 12 | —N⁺—CH(CH₃)₂ pyridinium | m.p. 160–183° C. (decomp.)<br>IR $\nu_{max}^{Nujol}$ (cm⁻¹): 3300, 1765, 1690, 1620, 1600 |
| 13 | —N⁺—CH₂OCH₃ pyridinium | m.p. 163–185° C. (decomp.)<br>IR $\nu_{max}^{Nujol}$ (cm⁻¹): 3250, 1760, 1690, 1625, 1600 |
| 14 | —N⁺—CH₂COONa pyridinium | m.p. 180–220° C. (decomp.)<br>IR $\nu_{max}^{Nujol}$ (cm⁻¹): 3300, 1770, 1690, 1630, 1600 |
| 15 | 2,6-dimethyl-N⁺—CH₂CH₂NHCOCH₃ pyridinium | m.p. 183° C. (decomp.)<br>IR $\nu_{max}^{Nujol}$ (cm⁻¹): 3300, 1770, 1690, 1655, 1620 |
| 16 | 2,6-dimethyl-N⁺—CH₂CH₂OH pyridinium | m.p. 175–215° C. (decomp.)<br>IR $\nu_{max}^{Nujol}$ (cm⁻¹): 3330, 1765, 1690, 1610 |
| 17 | N-ethyl pyridinium (N at 2-position), CH₂CH₃ | m.p. 160–175° C. (decomp.)<br>IR $\nu_{max}^{Nujol}$ (cm⁻¹): 3300, 1765, 1690, 1605 |

TABLE 1-continued

Structure:

H₂N–C(=S)–[thiazole]–C(=N–O–[pyrrolidinone])–CONH–[β-lactam-S]–CH₂SR² with COO⁻

| Ex. No. | R² | Properties |
|---|---|---|
| 18 | 1-methyl-pyridinium-3-yl with NHCOCH₃ | m.p.: >165° C. (decomp.)<br>Mass (m/e): 647 (M + 1)⁺<br>IR $\nu_{max}^{Nujol}$ (cm⁻¹): 3310, 1770, 1690, 1600, 1540 |
| 19 | 1-methyl-pyrimidinium with CH₃ | m.p.: >165° C. (decomp.)<br>Mass (m/e): 605 (M + 1)⁺<br>IR $\nu_{max}^{Nujol}$ (cm⁻¹): 3300, 1770, 1690, 1620, 1540 |
| 20 | 1-methyl-pyrimidinium | m.p.: >175° C. (decomp.)<br>IR $\nu_{max}^{Nujol}$ (cm⁻¹): 3320, 1770, 1690, 1600, 1550, 1530 |
| 21 | 1,2-dimethyl-5,6,7,8-tetrahydroquinolinium | m.p.: >185° C. (decomp.)<br>IR $\nu_{max}^{Nujol}$ (cm⁻¹): 3340, 1770, 1690, 1600 |
| 22 | 2,3-dimethyl-thiazolo[5,4-b]pyridinium | m.p.: >160° C. (decomp.)<br>Mass (m/e): 647 (M + 1)⁺<br>IR $\nu_{max}^{Nujol}$ (cm⁻¹): 3320, 1770, 1690, 1600, 1540 |
| 23 | 2,3-dimethyl-thiazolo[4,5-c]pyridinium | m.p.: >175° C. (decomp.)<br>IR $\nu_{max}^{Nujol}$ (cm⁻¹): 3330, 1770, 1690, 1625, 1600 |
| 24 | 1-methyl-pyridinium-4-yl with NH₂ | m.p. 182–205° C. (decomp.)<br>IR $\nu_{max}^{Nujol}$ (cm⁻¹): 3325, 3203, 1768, 1694, 1609 |
| 25 | 2,6-dimethyl-1-(CH₂CH₂NHCSNHCH₃)-pyridinium | m.p. 175–183° C. (decomp.)<br>IR $\nu_{max}^{Nujol}$ (cm⁻¹): 3300, 1770, 1695, 1615 |

TABLE 1-continued

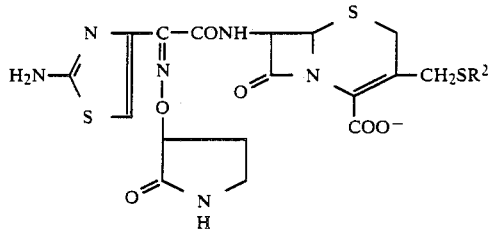

| Ex. No. | R² | Properties |
|---|---|---|
| 26 | [2,6-dimethyl-pyridinium]-N⁺—NHCOCH₃ | m.p. 185–215° C. (decomp.)<br>IR $\nu_{max}^{Nujol}$ (cm⁻¹): 3320, 1760, 1690, 1610 |
| 27 | [pyridinium]-N⁺—CH₂C(O)-N(morpholino) | m.p. 160–178° C. (decomp.)<br>IR $\nu_{max}^{Nujol}$ (cm⁻¹): 3280, 1765, 1695, 1650, 1630, 1600 |
| 28 | [pyridinium]-N⁺CH₂CONHCH(CH₃)₂ | m.p. 180–187° C. (decomp.)<br>IR $\nu_{max}^{Nujol}$ (cm⁻¹): 3300, 1760, 1670, 1625, 1600 |
| 29 | [3-CO₂CH₃-1-methyl-pyridinium] | m.p. 190–210° C. (decomp.)<br>IR $\nu_{max}^{Nujol}$ (cm⁻¹): 3340, 1770, 1735, 1690, 1600 |
| 30 | [pyridinium]-N⁺CH₂CH₂CH₂CONH₂ | m.p. 165–175° C. (decomp.)<br>IR $\nu_{max}^{Nujol}$ (cm⁻¹): 3350, 1770, 1670, 1630, 1600 |
| 31 | [2,6-dimethyl-pyridinium]-N⁺—CH₂CH₂NH₂ | m.p. >165° C. (decomp.)<br>Mass (m/e): 647 (M + 1)⁺<br>IR $\nu_{max}^{Nujol}$ (cm⁻¹): 3340, 1770, 1680, 1610, 1550, 1530 |
| 32 | [pyridinium]-N⁺—CH₂CSNH₂ | m.p. >175° C. (decomp.)<br>Mass (m/e): 649 (M + 1)⁺<br>IR $\nu_{max}^{Nujol}$ (cm⁻¹): 3320, 1760, 1680, 1620, 1590, 1530 |
| 33 | [2,6-dimethyl-pyridinium]-N⁺—CH₂CONH₂ | m.p. >190° C. (decomp.)<br>Mass (m/e): 661 (M + 1)⁺<br>IR $\nu_{max}^{Nujol}$ (cm⁻¹): 3330, 1770, 1690, 1620, 1550, 1530 |
| 34 | [pyridinium]-N⁺—CH₂CSNHCH₃ | m.p. >175° C. (decomp.)<br>Mass (m/e): 663 (M + 1)⁺<br>IR $\nu_{max}^{Nujol}$ (cm⁻¹): 3300, 1770, 1690, 1630, 1540 |

TABLE 1-continued

[Structure: cephalosporin with aminothiazole oxime group, pyrrolidinone-O substituent, and CH₂SR² at 3-position]

| Ex. No. | R² | Properties |
|---|---|---|
| 35 | [pyridazinium-N⁺-CH₃] | m.p. >175° C. (decomp.)<br>Mass (m/e): 591 (M + 1)⁺<br>IR $\nu_{max}^{Nujol}$ (cm⁻¹): 3320, 1765, 1690, 1630, 1600, 1530 |
| 36 | [2,6-dimethylpyridinium-N⁺-CH₂CH₂NHC(O)NHCH₃] | m.p. >180° C. (decomp.)<br>IR $\nu_{max}^{Nujol}$ (cm⁻¹): 3300, 1770, 1690, 1660, 1610 |
| 37 | [2,6-dimethylpyridinium-N⁺-CH₃] | m.p. >175° C. (decomp.)<br>IR $\nu_{max}^{Nujol}$ (cm⁻¹): 3320, 1765, 1690, 1615 |
| 38 | [2,6-dimethylpyridinium-N⁺-CH₂CH₂OC(O)NHCH₃] | m.p. >170° C. (decomp.)<br>IR $\nu_{max}^{Nujol}$ (cm⁻¹): 3300, 1770, 1700, 1615 |
| 39 | [pyridinium-N⁺CH₂CONHCH₂CH=CH₂] | m.p. >175° C. (decomp.)<br>IR $\nu_{max}^{Nujol}$ (cm⁻¹): 3260, 1765, 1680, 1630, 1600 |
| 40 | [pyridinium-N⁺CH₂CONHNH₂] | m.p. >200° C. (decomp.)<br>IR $\nu_{max}^{Nujol}$ (cm⁻¹): 3300, 1760, 1695, 1625 |
| 41 | [pyridazinium with CH₃, ⁺N—N—CH₃, CH₃] | m.p. 155–165° C. (decomp.)<br>IR $\nu_{max}^{Nujol}$ (cm⁻¹): 3350, 1765, 1690, 1600 |
| 42 | [pyridinium-N⁺CH₂CON(CH₃)₂] | m.p. 175–180° C. (decomp.)<br>IR $\nu_{max}^{Nujol}$ (cm⁻¹): 3300, 1770, 1690, 1660, 1630 |

TABLE 1-continued

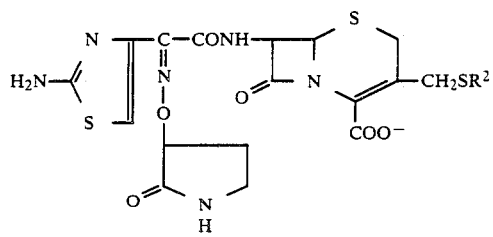

| Ex. No. | R² | Properties |
|---|---|---|
| 43 | —[2,6-dimethylpyridinium]—CH₂CH₂NHCOC(CH₃)₃ (with C=O) | m.p. >175° C. (decomp.)<br>Mass (m/e): 747 (M + 1)<br>IR $\nu_{max}^{Nujol}$ (cm⁻¹): 3330, 1770, 1690, 1610, 1530 |
| 44 | —[pyridinium]—CH₃ | m.p. >165° C. (decomp.)<br>IR $\nu_{max}^{Nujol}$ (cm⁻¹): 3340, 1765, 1690, 1600 |
| 45 | —[pyridinium]—N⁺—CH₂CH₂CONH₂ | m.p. >180° C. (decomp.)<br>IR $\nu_{max}^{Nujol}$ (cm⁻¹): 3340, 1760, 1670, 1620 |
| 46 | —[2-carbamoylpyridinium]—N⁺—CH₃, CONH₂ | m.p. >175° C. (decomp.)<br>Mass (m/e): 633 (M⁺ + 1)<br>IR $\nu_{max}^{Nujol}$ (cm⁻¹): 3320, 1765, 1690, 1610 |
| 47 | —[2-carboxylatepyridinium]—N⁺—CH₃, CO₂K | m.p. >175° C. (decomp.)<br>IR $\nu_{max}^{Nujol}$ (cm⁻¹): 3380, 1760, 1690, 1650, 1610 |
| 48 | —[pyridinium]—N⁺CH₂CH₂CH₂C(=S)NH₂ | m.p. >168° C. (decomp.)<br>Mass (m/e): 677 (M + 1)⁺<br>IR $\nu_{max}^{Nujol}$ (cm⁻¹): 3320, 1770, 1690, 1630, 1600, 1530 |
| 49 | —[pyridinium]—N⁺CH₂CONHOH | m.p. >195° C. (decomp.)<br>Mass (m/e): 649 (M + 1)⁺<br>IR $\nu_{max}^{Nujol}$ (cm⁻¹): 3320, 3200, 1770, 1690, 1630, 1600, 1540 |
| 50 | —[pyridinium]—N⁺—pyrrolidinone | m.p. >185° C. (decomp.)<br>Mass (m/e): 659 (M + 1)⁺<br>IR $\nu_{max}^{Nujol}$ (cm⁻¹): 3320, 1760, 1700, 1620, 1600, 1530 |
| 51 | —[pyridazinium]—N⁺—CH₃ | m.p. >140° C. (decomp.)<br>Mass (m/e): 591 (M + 1)⁺<br>IR $\nu_{max}^{Nujol}$ (cm⁻¹): 3320, 3200, 1760, 1680, 1600, 1580 |

TABLE 1-continued

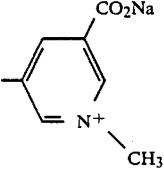

| Ex. No. | R² | Properties |
|---|---|---|
| 52 | 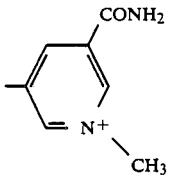 3-(CO₂Na)-1-CH₃-pyridinium | m.p. >210° C. (decomp.)<br>Mass (m/e): 656 (M + 1)⁺<br>IR $\nu_{max}^{Nujol}$ (cm⁻¹): 3380, 1760, 1690, 1630, 1600, 1540 |
| 53 | 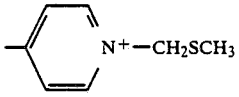 3-(CONH₂)-1-CH₃-pyridinium | m.p. >195° C. (decomp.)<br>Mass (m/e): 633 (M + 1)⁺<br>IR $\nu_{max}^{Nujol}$ (cm⁻¹): 3320, 3200, 1760, 1680, 1600, 1530 |
| 54 | 1-(CH₂SCH₃)-pyridinium | m.p. 160–175° C. (decomp.)<br>IR $\nu_{max}^{Nujol}$ (cm⁻¹): 3320, 1700, 1690 |
| 55 | 1-(CH₂CN)-pyridinium | m.p. 170–190° C. (decomp.)<br>IR $\nu_{max}^{Nujol}$ (cm⁻¹): 3330, 1765, 1690, 1625 |
| 56 | 1-((CH₂)₄CONH₂)-pyridinium | m.p. 160–165° C. (decomp.)<br>Mass (m/e): 675 (M + 1)⁺<br>IR $\nu_{max}^{Nujol}$ (cm⁻¹): 3400, 1760, 1660, 1620, 1600, 1530 |
| 57 | 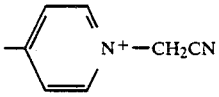 1-(CH₂-(5-methyl-1,3,4-thiadiazol-2-yl))-pyridinium | m.p. 155–165° C. (decomp.)<br>Mass (m/e): 688 (M + 1)⁺ |
| 58 | 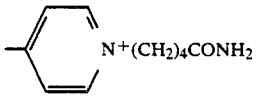 1-(CH₂-C₆H₄-CONH₂)-pyridinium | m.p. 170–184° C. (decomp.)<br>Mass (m/e): 709 (M + 1)⁺ |
| 59 | 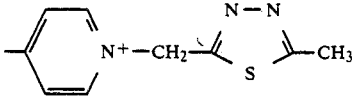 1-(CH(CH₃)CONH₂)-pyridinium | m.p. >182° C. (decomp.)<br>IR $\nu_{max}^{Nujol}$ (cm⁻¹): 3330, 1765, 1690, 1620 |
| 60 | 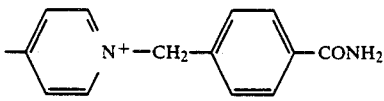 2-(CSNH₂)-1-CH₃-pyridinium | m.p. >190° C. (decomp.)<br>IR $\nu_{max}^{Nujol}$ (cm⁻¹): 3320, 1765, 1690, 1610 |
| 61 | 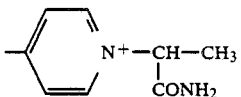 1-(CH₂C(=S)N(CH₃)₂)-pyridinium | m.p. 170° C. (decomp.)<br>Mass (m/e): 677 (M + 1)⁺<br>IR $\nu_{max}^{Nujol}$ (cm⁻¹): 3360, 1770, 1690, 1630, 1600, 1530 |

TABLE 1-continued

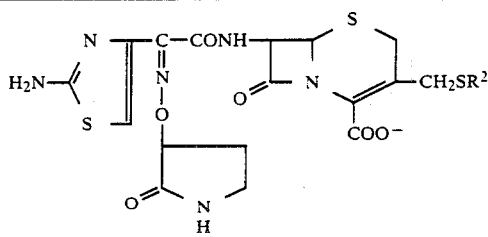

| Ex. No. | R² | Properties |
|---|---|---|
| 62 | ![4-(N-methyl)pyridinio] with NHCHO substituent | m.p. >193° C. (decomp.)<br>Mass (m/e): 633 (M + 1)⁺<br>IR $\nu_{max}^{Nujol}$ (cm⁻¹): 3340, 1760, 1690, 1580, 1530 |
| 63 | pyridinio-CH₂C(=S)-N(morpholino) | m.p. 178–183° C. (decomp.)<br>IR $\nu_{max}^{Nujol}$ (cm⁻¹): 3280, 1770, 1690, 1630, 1600 |
| 64 | pyridinio-CH₂CONHC(CH₃)₃ | m.p. 175–192° C. (decomp.)<br>IR $\nu_{max}^{Nujol}$ (cm⁻¹): 3260, 1750, 1680, 1630, 1540 |

TABLE 2

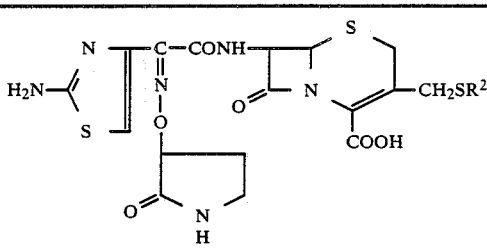

| Ex. No. | R² | Properties |
|---|---|---|
| 65 | 4-pyridyl | (potassium salt)<br>m.p. 210–220° C. (decomp.)<br>Mass (m/e): 614 (M)<br>IR $\nu_{max}^{Nujol}$ (cm⁻¹): 3340, 3200, 1765, 1700, 1600, 1580, 1540 |
| 66 | 2-pyridyl | (sodium salt)<br>m.p. 190–220° C. (decomp.)<br>Mass (m/e): 598 (M)<br>IR $\nu_{max}^{Nujol}$ (cm⁻¹): 3300, 3200, 1760, 1690, 1600, 1575, 1530 |
| 67 | thiazolo[5,4-b]pyridin-2-yl | (potassium salt)<br>m.p. 170–195° C. (decomp.)<br>IR $\nu_{max}^{Nujol}$ (cm⁻¹): 3320, 3200, 1765, 1695, 1595 |

The compounds of Example 66 and 67 are each treated in the same manner as in Example 6, thereby giving 7β-{(Z)-2-(2-aminothiazol-4-yl)-2-[((3S)-2-oxopyrrolidin-3-yl)oxyimino]acetamido}-3-(1-methyl-2-pyridinio)thiomethyl-3-cephem-4-carboxylate and 7β-{(Z)-2-(2-aminothiazol-4-yl)-2-[((3S)-2-oxopyrrolidin-3-yl)oxyimino]acetamido}-3-(1-methyl-thiazolo[5,4-b]pyridinium-2-yl)thiomethyl-3-cephem-4-carboxylate, respectively. The physico-chemical properties of these products are each identical with those of the compouds of Examples 2 and 22, respectively.

REFERENCE EXAMPLE 1

A mixture of 7.56 g of 4-chloropyridine and 4.83 g of allyl bromide is stirred at room temperature. Then acetone is added to the reaction mixture, and the precipitate thus obtained is added to 36 ml of 18% aqueous solution of NaSH with cooling, and the resulting mixture is stirred at room temperature. After the reaction, the crystals precipitated are filtered, thereby giving 2.81 g of 1-(4-pyridyl)-4-thiopyridone melting at 212°–217° C. (decomp.).

The filtrate is then extracted with chloroform, and the chloroform layer is dried and concentrated. The concentrate is purified, giving 1.22 g of 1-allyl-4-thiopyridone melting at 77°–79° C. and 0.18 g of 1-(4-pyridyl)-4-thiopyridone.

REFERENCE EXAMPLE 2–6

The compounds listed in Table 4 below are prepared from the corresponding starting materials following the general procedure of Reference Example 1.

TABLE 4

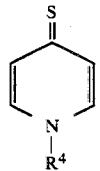

| Ref. Ex. No. | R⁴ | Melting point (°C.) |
|---|---|---|
| 2 | —CH₂CH₃ | 113–114 |

TABLE 4-continued

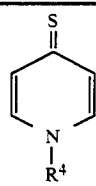

| Ref. Ex. No. | R⁴ | Melting point (°C.) |
|---|---|---|
| 3 | —CH₂CH₂CH₃ | 103–104.5 (recrystallized from isopropyl ether) |
| 4 | —CH(CH₃)₂ | 90.5–91.5 |
| 5 | —CH₂SCH₃ | 136–137 (decomp.) |
| 6 | —CH₂OCH₃ | 95–97 |

REFERENCE EXAMPLE 7

A 1.03 g quantity of 1-methyl-2-chloro-5-(acetylamino)pyridinium iodide is dissolved in water with heating. After cooling, 2 ml of 18% aqueous solution of NaSH was added to the solution, and the mixture is allowed to react at room temperature. The crystals precipitated are filtered and purified, giving 0.34 g of 1-methyl-5-(acetylamino)-2-thiopyridone. m.p. 135°–159° C. (decomp.)

REFERENCE EXAMPLE 8

A mixture of 2.41 g of 1-(2-(dimethylamino)ethyl)-4-pyridone and 3.63 g of Lawesson's reagent in dimethoxyethane is stirred, refluxed and further allowed to react at room temperature overnight, and the solvent is evaporated off. The residue is purified, giving 2.02 g of 1-(2-(dimethylamino)ethyl)-4-thiopyridone. m.p. 138°–139° C.

REFERENCE EXAMPLES 9-12

The compounds listed in the following Table 5 are prepared from the corresponding starting materials following the general procedure of Reference Example 8.

TABLE 5

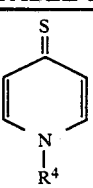

| Ref. Ex. No. | R⁴ | Melting point (°C.) |
|---|---|---|
| 9 | —CH₂CN | 213–215 (decomp., recrystallized from water-methanol) |
| 10 | (cyclic structure with NH and C=O) | 238–239 (decomp.) |
| 11 | —CH(CH₃)CONH₂ | 211–212 (decomp., recrystallized from water) |
| 12 | —(CH₂)₄CONH₂ | 161–162 (recrystallized from methanol) |

REFERENCE EXAMPLE 13

In methanol is dissolved 2.40 g of 1-ethoxycarbonyl-methyl-4-thiopyridone. To this solution is added 50 ml of 30% solution of methylamine in methanol, and the mixture is allowed to react at room temperature. The solvent is evaporated off and the residue is recrystallized from ethanol, giving 1.85 g of 1-((N-methylcarbamoyl)methyl)-4-thiopyridone melting at 184°–185° C.

REFERENCE EXAMPLES 14-23

The compounds listed in Table 6 below are prepared from the corresponding starting materials following the general procedure of Reference Example 13.

TABLE 6

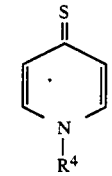

| Ref. Ex. No. | R⁴ | Melting point (°C.) |
|---|---|---|
| 14 | —CH₂CONHCH₂CH=CH₂ | 156–162 |
| 15 | —CH₂CON(morpholino)O | 224–227 (decomp., recrystallized from ethanol) |
| 16 | —CH₂CONHCH(CH₃)₂ | 194–195 (decomp., recrystallized from acetone) |
| 17 | —CH₂CONHNH₂ | 241–245 (decomp., recrystallized from water-ethanol) |
| 18 | —CH₂CON(CH₃)₂ | 180–182 (decomp., recrystallized from ethanol) |
| 19 | —CH₂CONHOH | 164–167 (decomp., recrystallized from water-ethanol) |
| 20 | —CH₂CONHC(CH₃)₃ | 183–186 (decomp.) |
| 21 | —CH₂CONH₂ | 241–250 (decomp., recrystallized from water) |
| 22 | —CH₂CH₂CH₂CONH₂ | 143–144 (recrystallized from methanol) |
| 23 | —CH₂CH₂CONH₂ | 206–207 (recrystallized from methanol) |

REFERENCE EXAMPLE 24

In methanol is dissolved 2.5 g of 1-ethoxycarbonyl-methyl-4-thiopyridone. To the solution is added 13 ml of 1N NaOH and hydrolysis is effected, giving 2.27 g of sodium salt of 1-carboxymethyl-4-thiopyridone. m.p. 279°–280° C. (decomp.).

REFERENCE EXAMPLES 25-33

The corresponding starting materials are treated in the same manner as in Reference Example 24, or are subjected to an acylation or a carbamoyl- or ureido-forming reaction in a conventional manner, thereby giving the compounds listed in the following Table 7.

TABLE 7

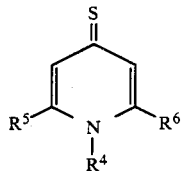

| Ref. Ex. No. | Product | Melting point (°C.) |
|---|---|---|
| 25 | $R^4 = -CH_2CH_2NHCOCH_3$<br>$R^5 = R^6 = CH_3$ | 223–224 (recrystallized from acetonitrile) |
| 26 | $R^4 = -CH_2CH_2OCONHCH_3$<br>$R^5 = R^6 = CH_3$ | 179–180 (recrystallized from acetonitrile) |
| 27 | $R^4 = -CH_2CH_2NH\overset{\overset{S}{\|}}{C}NHCH_3$<br>$R^5 = R^6 = CH_3$ | 209–211 (decomp.) |
| 28 | $R^4 = -CH_2CH_2NH\overset{\overset{O}{\|}}{C}NHCH_3$<br>$R^5, R^6 = CH_3$ | 193–194 (decomp.) |
| 29 | $R^4 = -CH_2CH_2NH\overset{\overset{O}{\|}}{C}O(CH_3)_3$<br>$R^5 = R^6 = CH_3$ | 213–214 (decomp., recrystallized from acetone) |
| 30 | ![structure with S=, N-CH3, NH2] | 182–184 (decomp., recrystallized from methanol-ether) |
| 31 | $R^4 = -CH_2-\!\!\!\!\text{⌬}\!\!\!\!-CONH_2$<br>$R^5 = R^6 = H$ | 245–247 (decomp., recrystallized from water-methanol) |
| 32 | $R^4 = -CH_3, R^5 = H$<br>$R^6 = CONH_2$ | 230 (decomp.) |
| 33 | $R^4 = -CH_3, R^5 = H$<br>$R^6 = COOH$ | 87–90 |

REFERENCE EXAMPLE 34

(1) A mixture of 8.10 g of 2-mercapto-4-methylpyrimidine hydrochloride, 7.88 g of methyl iodide and 13.82 g of potassium carbonate in methanol is allowed to react in the dark. The insoluble materials are filtered off, and the solvent is evaporated off. The residue is dissolved in water and extracted with methylene chloride. The extract is washed and dried, and the solvent is evaporated off. The resulting residue (4.75 g) is mixed with 4.63 g of methyl iodide in acetonitrile, and the mixture is allowed to react in a sealed tube at 100° C. After the reaction, the solvent is evaporated off. The residue is purified, giving 5.14 g of 1,4-dimethyl-2-methylthiopyrimidinium iodide.

(2) To a solution of the above product (3.49 g) in 40 ml of water is added dropwise a solution of 4.46 g of sodium sulfide nonahydrate in 15 ml of water, and the mixture is allowed to react. The reaction mixture is extracted with methylene chloride and the extract is dried. The solvent is evaporated off and the residue is purified, giving 2 g of 3,6-dimethylpyrimidine-2(3H)-thione. m.p. 138°–140° C.

REFERENCE EXAMPLES 35 and 36

The compounds listed below are prepared from the corresponding starting materials following the general procedure of Reference Example 34.
(35) 1-methyl-1H-thiazolo[5,4-b]pyridine-2-thione m.p. 258°–260.5° C.
(36) 3-methyl-3H-thiazolo[4,5-c]pyridine-2-thione m.p. 265°–266° C. (decomp., recrystallized from methanol)

REFERENCE EXAMPLE 37

To a suspension of 6.7 g of 1,2-dimethyl-5,6,7,8-tetrahydro-4-quinolone in dimethoxyethane are added 15.27 g of Lawesson's reagent and 100 ml of pyridine, and the mixture is refluxed. The solvent is evaporated off and the residue is dissolved in chloroform. The chloroform solution is washed, dried and evaporated to dryness. The residue is purified, giving 5.29 g of 1,2-dimethyl-5,6,7,8-tetrahydro-4-thioquinolone. m.p. 209°–210° C. (recrystallized from ether isopropyl ether).

REFERENCE EXAMPLE 38

A 3.0 g quantity of 2,6-dimethyl-γ-thiopyrone is suspended in ethanol. To the suspension is added 5.2 g of ethanolamine, and the reaction is effected. Then the solvent is evaporated off, and the residue is purified, giving 2.50 g of 1-(2-hydroxyethyl)-2,6-dimethyl-4-thiopyridone. m.p. 212°–213° C. (recrystallized from ethanol).

REFERENCE EXAMPLES 39–41

The compounds listed in Table 8 below are prepared from the corresponding starting materials following the general procedure of Reference Example 38.

TABLE 8

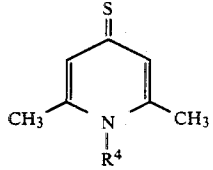

| Ref. Ex. No. | $R^4$ | Melting point (°C.) |
|---|---|---|
| 39 | $-NHCOCH_3$ | 251–253 (decomp., recrystallized from acetonitrile) |
| 40 | $-(CH_2)_2NH_2$ | 174–175 (recrystallized from isopropanol) |
| 41 | $-CH_3$ | 264–266 (decomp., recrystallized from acetonitrile) |

REFERENCE EXAMPLE 42

A solution of 5.31 g of 1-cyanomethyl-4-pyridone in POCl$_3$ is refluxed and then the POCl$_3$ is evaporated off. To the residue is added ice water, followed by addition of 18% an aqueous solution of NaSH. The mixture is stirred. The crystals thus precipitated are filtered, giving 2.07 g of 1-(thiocarbamoyl)methyl-4-thiopyridone. m.p. 195°–197° C. (decomp., recrystallized from water-containing mathanol).

REFERENCE EXAMPLE 43

Following the general procedure of Reference Example 42 and using the corresponding starting materials, 1,2,3-trimethyl-5-thioxo-3-pyrazoline is prepared. m.p. 143°–146° C. (recrystallized from isopropanol).

REFERENCE EXAMPLE 44

A solution of 2.15 g of 1-(N-methylcarbamoyl)methyl-4-thiopyridone, 4.77 g of Lawesson's reagent and 70 ml of pyridine in dimethoxyethane is refluxed. The solvent is evaporated off, and the residue is purified, thereby giving 1.61 g of 1-(N-methyl(thiocarbamoyl))methyl-4-thiopyridone. m.p. 178°–179° C. (decomp., recrystallized from ethanol).

REFERENCE EXAMPLES 45–48

The compounds listed in Table 9 below are prepared from the corresponding starting materials following the general procedure of Reference Example 44.

TABLE 9

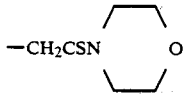

| Ref. Ex. No. | R$^4$ | R$^5$ | Melting point (°C.) |
|---|---|---|---|
| 45 | —CH$_2$CSN(CH$_3$)$_2$ | H | 197–200 (decomp., recrystallized from methanol-ether) |
| 46 | —(CH$_2$)$_3$CSNH$_2$ | H | 196–198 (decomp., recrystallized from water-methanol) |
| 47 | —CH$_2$CSN⟨morpholino⟩ | H | 206–208 (decomp., recrystallized from methanol-ether) |
| 48 | —CH$_3$ | —CSNH$_2$ | 205–210 (decomp.) |

REFERENCE EXAMPLE 49

The corresponding materials are treated first in the same manner as in Reference Example 26 and then in the same manner as in Reference Example 4, giving 1-carbamoylmethyl-2,6-dimethyl-4-thiopyridone. m.p. >251° C. (decomp.).

REFERENCE EXAMPLE 50

(1) A solution of 2.02 g of 5-(p-methoxybenzylthio)-nicotinic acid in hydrochloric acid-methanol is refluxed. The reaction mixture is concentrated. To the residue is added a mixture of chloroform and water. The mixture is extracted with chloroform. The chloroform layer is dried and evaporated to dryness. The resulting residue is recrystallized from isopropyl ether, giving methyl 5-(p-methoxybenzylthio)nicotinate melting at 72°–74° C.

(2) A 2.07 g portion of the methyl 5-(p-methoxybenzylthio)nicotinate prepared above and 8.1 g of methyl iodide are dissolved in acetone and are allowed to react. The reaction mixture is concentrated under reduced pressure, giving 2.86 g of crystals.

(3) A 517 mg portion of the crystals obtained above, 6 ml of formic acid and 1.16 g of Hg(OCOCH$_3$)$_2$ are allowed to react in water. The resulting precipitate is filtered off. Hydrogen sulfide gas is passed through the filtrate, and the resulting precipitate is filtered off. The filtrate is extracted with chloroform-methanol, and the extract is dried. The solvent is evaporated off, and the residue is purified, giving 49 mg of 1-methyl-3-mercapto-5-methoxycarbonylpyridinium inner salt. m.p. 120°–123° C. (decomp., recrystallized from methanol-ether).

REFERENCE EXAMPLES 51–54

The compounds listed in Table 10 below are prepared from the corresponding starting materials following the general procedure of Reference Example 50.

TABLE 10

| Ref. Ex. No. | Product | Physical property |
|---|---|---|
| 51 | pyridinium with —S— at 5, N$^+$—CH$_3$ | IR $\nu_{max}^{Film}$ (cm$^{-1}$): 3430, 1640 |
| 52 | pyridinium with HS— at 5, —COO$^-$ at 3, N$^+$—CH$_3$ | m.p. 197–201° C. (decomp., recrystallized from methanol-ether) |
| 53 | pyridinium with —S— at 5, —COONH$_2$ at 3, N$^+$—CH$_3$ | m.p. 209–211° C. (decomp., recrystallized from water) |
| 54 | pyridinium with —S— at 5, —NHCHO at 3, N$^+$—CH$_3$ | m.p. 174–178° C. |

REFERENCE EXAMPLE 55

A mixture of 2.50 g of 1-(N-acetamidocarbamoyl)-methyl-4-thiopyridone (prepared from 1-(N-aminocarbamoyl)methyl-4-thiopyridone), 5 g of Lawesson's reagent and 100 ml of pyridine is refluxed. The pyridine is evaporated off, and the residue is purified, giving 1-(5-methyl-1,3,4-thiadiazol-2-yl)methyl-4-thiopyridone. m.p. 195°–197° C. (decomp., recrystallized from acetone-ether).

We claim:

1. A cephalosporin compound of the formula

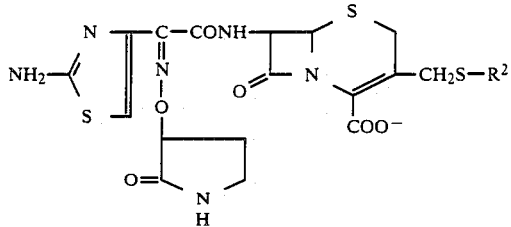 (I)

wherein: $R^2$ is a group of the formula

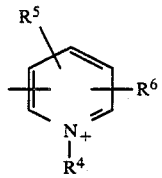

$R^4$ is a lower alkenyl group, a lower alkyl group or a lower alkyl group substituted with a member selected from the group consisting of cyano, lower alkylthio, 2-(lower alkyl)-1,3,4-thiadiazol-5-yl, carbamoyl, thiocarbamoyl, and N-lower alkyl(thiocarbamoyl), and $R^5$ and $R^6$ are each a hydrogen atom or a lower alkyl group, or a pharmaceutically acceptable salt thereof.

2. A compound according to claim 1, wherein $R^2$ is a group of the formula

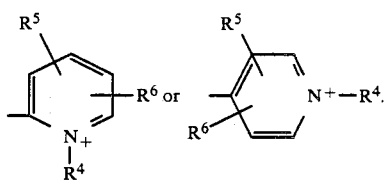

3. A compound according to claim 2, wherein $R^4$ is a member selected from the group consisting of allyl, methyl, ethyl, cyanomethyl, methylthiomethyl, (2-methyl-1,3,4-thiadiazol-5-yl)methyl, carbamoylmethyl, carbamoylbutyl, thiocarbamoylmethyl and N-methyl(thiocarbamoyl)methyl and $R^5$ and $R^6$ are hydrogen or methyl.

4. A compound according to claim 3, which is selected from the group consisting of 7β-[(Z)-2-(2-aminothiazol-4-yl)-2-[((3S)-2-oxopyrrolidin-3-yl)oxyimino]acetamido]-3-(1-methyl-4-pyridinio)thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1-methyl-2-pyridinio)thiomethy-3-cephem-4-carboxylate, 7β-[(Z)-2-(2-aminothiazol-4-yl)-2-[((3S)-2-oxopyrrolidin-3-yl)oxyimino]acetamido]-3-(1-allyl-2-pyridinio)-thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1-thiocarbamoylmethyl-4-pyridinio)thiomethyl-3-cephem-4-carboxylate, 7β-[(Z)-2-(2-aminothiazol)-4-yl)-2-[((3S)-2-oxopyrrolidin-3-yl)oxyimino]acetamido]-3-(1-(N-methyl(thiocarbamoyl)methyl)-4-pyridinio)thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1-allyl-4-pyridinio)-thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1-carbamoylmethyl-4-pyridinio)thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1-ethyl-4-pyridinio)thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1,2,6-trimethyl-4-pyridinio)thiomethyl-3-cephem-4-carboxylate, 7β-[(Z)-2-(2-aminothiazol-4-yl)-2-[((3S)-2-oxopyrrolidin-3-yl)oxyimino]acetamido]-3-1-methylthiomethyl-4-pyridinio)thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1-cyanomethyl-4-pyridinio)thiomethyl-3-cephem-4-carboxylate, 7β-[(Z)-2-(2-aminothiazol-4-yl)-2-[((3S)-2-oxopyrrolidin-3-yl)oxyimino]acetamido]-3-(1-(4-carbamoylbutyl)-4-pyridinio)thiomethyl-3-cephem-4-carboxylate, and 7β-[(Z)-2-(2-aminothiazol-4-yl)-2-[((3S)-2-oxopyrrolidin-3-yl)oxyimino]acetamido]-3-(1-((2-methyl-1,3,4-thiadiazol-5-yl)methyl)-4-pyridinio)thiomethyl-3-cephem-4-carboxylate, or a pharmaceutically acceptable salt thereof.

5. A pharamaceutical composition comprising an antimicrobially effective amount of the cephalosporin compound of claim 1 or a pharmaceutically acceptable salt thereof, and a pharmaceutically acceptable carrier therefor.

6. A method of treating microbial infections in a mammal comprising administering to said mammal an antimicrobially effective amount of the cephalosporin compound of claim 1 or a pharmaceutically acceptable salt thereof.

7. The method according to claim 6, wherein said microbial infection comprises gram-positive or gram-negative bacteria.

8. The compound according to claim 1, wherein said pharmaceutically acceptable salt includes a member selected from the group consisting of sodium, potassium, calcium, magnesium aluminum, triethylamine, pyridine, ethanolamine, triethanolamine, dicyclohexylamine, hydrochloric acid, sulfuric acid, hydrobromic acid, oxalic acid, tartaric acid, glycine, lysine, arginine, aspartic acid and glutamic acid.

9. The method according to claim 6, wherein said cephalosporin compound is administered orally or parenterally.

* * * * *